(12) United States Patent
Robichaud

(10) Patent No.: US 6,610,720 B2
(45) Date of Patent: Aug. 26, 2003

(54) METHOD FOR TREATING OR PREVENTING EMESIS

(75) Inventor: Annette Robichaud, Montreal (CA)

(73) Assignee: Merck Frosst Canada & Co., Kirkland (CA)

( * ) Notice: Subject to any disclaimer, the term of this patent is extended or adjusted under 35 U.S.C. 154(b) by 0 days.

(21) Appl. No.: 09/939,175

(22) Filed: Aug. 24, 2001

(65) Prior Publication Data

US 2002/0045565 A1 Apr. 18, 2002

Related U.S. Application Data

(60) Provisional application No. 60/227,640, filed on Aug. 24, 2000.

(51) Int. Cl.[7] ............................................. A61K 31/415
(52) U.S. Cl. ...................................... 514/385; 514/227.2
(58) Field of Search .............................. 514/385, 227.2

(56) References Cited

U.S. PATENT DOCUMENTS 5,576,317 A  * 11/1996 Gonsalves ............... 514/231.2
5,719,185 A  *  2/1998 Bountra et al. ............. 514/567
2001/0049368 A1  * 12/2001 Reines et al. ............ 514/235.8

OTHER PUBLICATIONS

CAPLUS DN 121:291791, Eisenach, Expert Opin. Invest. Drugs (1994), 3 (10), 1005–10 (abstract only).*

CAPLUS DN 117:245969, Lang et al., J. Pharmacol. Exp. Ther. (1992), 263(1), 395–403 (abstract only).*

CAPLUS DN 124:250441, Itoh et al., Nippon Juishikai Zasshi (1996), 49(2), 107–9 (abstract only).*

CAPLUS DN 120:153491, Nakamura et al., Iwate Daigaku Nogakubu Hokoku (1993), 21(3), 201–13 (abstract only).*

CAPLUS DN 111:209005, Lucot et al., Pharmacol. Biochem. Behav. (1989), 33(3), 627–31 (abstract only).*

* cited by examiner

*Primary Examiner*—Dwayne C. Jones
*Assistant Examiner*—C. Delacroix-Muirheid
(74) *Attorney, Agent, or Firm*—J. Eric Thies; Melvin Winokur

(57) ABSTRACT

Alpha-2 adrenoreceptor agonists are useful for the treatment and/or prevention of emesis in patients.

15 Claims, No Drawings

METHOD FOR TREATING OR PREVENTING EMESIS

CROSS REFERENCE TO RELATED APPLICATIONS

This application claims the benefit of Provisional Application No. 60/227,640, filed Aug. 24, 2000.

BACKGROUND OF THE INVENTION

The adrenergic receptors were first divided into $\alpha$ and $\beta$ classes by Ahlquist in 1948. This division was based on a pharmacological characterisation. Both the $\alpha$-receptors and the $\beta$-adrenoceptors have since been subdivided into $\alpha_1$ and $\alpha_2$ and $\beta_1$ and $\beta_2$.

There are three known sub-types of the $\alpha_2$-adrenergic receptor population, designated $\alpha_{2A}$, $\alpha_{2B}$ and $\alpha_{2C}$. All $\alpha_2$-adrenergic receptor subtypes affect the same effector systems, i.e., inhibition of adenylate cyclase, activation of receptor-operated $K^+$ channels, and inhibition of voltage-sensitive $Ca^{2+}$ channels.

Alpha-2 adrenergic agonists are useful for treating a variety of disorders including: respiratory disorders (e.g., asthma, nasal congestion, congestive obstructive pulmonary disease (COPD), cough, cystic fibrosis), gastrointestinal disorders (e.g., diarrhoea, irritable bowel syndrome), ocular disorders (e.g., glaucoma), cardiovascular disorders (e.g., myocardial ischemia, shock, arrhythmias, angina, congestive heart failure), benign prostatic hypertrophy and migraine. Many compounds disclosed in the art as alpha-2 adrenoceptor agonists are not alpha-2 adrenoceptor selective (e.g., they interact with other alpha receptors such as alpha-1 adrenoceptors). Alpha-2 adrenoceptor selectivity is desirable when treating alpha-2 associated or alpha-2 mediated disorders. For example, alpha-2 adrenergic agonists that possess significant alpha-1 adrenergic effects are known to cause cardiovascular side effects such as hypertension.

Alpha-2 adrenoceptor agonists such as clonidine or xylazine are known to cause emesis in cats and dogs (Hikasa et al, *J. Pharmacol. Exp. Ther.* (1989) 261, 746–754; Hikasa et al, *Eur. J. Pharmacol.* (1992) 229, 241–251; Hikasa et al, *Am. J. Vet. Res.* (1992) 50, 1348–1351; and Japundzic-Zigon et al, *Pharmacol. Res.* (1997) 35, 287–297. In both species, clonidine has been shown to be the most potent emetic alpha-2 adrenoceptor agonist with an $ED_{50}$ of 25 $\mu g/kg$ (i.m.) in dogs and 0.075 $\mu g/kg$ (i.c.v.) in cats (Hikasa et al, 1992, supra). This effect is thought to be mediated predominantly through the activation of alpha-2 adrenoceptors, since drugs with alpha-2 adrenoceptor antagonistic activity, such as yohimbine, were reported to abolish clonidine-induced emesis in these species (Hikasa et al, 1989, and 1992; and Japundzic-Zigon et al, 1997, supra).

Surprisingly, however, the inventors have found that these previously reported observations in the cat and dog are inconsistent with the effects of alpha-2 adrenoceptor agonists and antagonists in the ferret. It is widely recognized that the ferret is an excellent model for studying the emetic response with considerable predictability of the effects of anti-emetic agents in man. The inventors have found that administration of yohimbine alone to ferrets caused unexpected retching and vomiting. Moreover, in contrast to what has been reported in cats and dogs, clonidine did not trigger emesis in ferrets even at doses of 250 $\mu g/kg$ (i.e. 10 times the $ED_{50}$ reported in dogs). It is of interest to note that pigeons have been reported to respond similarly to the administration of yohimbine or clonidine (Khandker et al, *Pharmacol. Res.* (1994) 29, 383–387) but there is no literature precedent for emesis in pigeons as a predictor for the effects of anti-emetic agents in man. In humans, nausea and vomiting has been reported following parenteral administration of yohimbine (Weiner at page 190 in Goodman & Gilman's "The Pharmacological Basis of Therapeutics, MacMillan Publishing Company, New York 1985).

The mechanism by which yohimbine activates the emetic reflex is not clear. In the studies described herein, the emetic action of yohimbine in the ferret can not be explained by an unspecific effect of yohimbine since similar responses were noted with two other potent and selective alpha-2 adrenoceptor antagonists, namely MK-912 and MK-467 (Pettibone et al, 1987, supra; Clineschmidt et al, 1988, supra). It also appears that both a peripheral and a central locus of action are involved. Inhibition of the alpha-2 adrenoceptor either with a peripherally active antagonist, MK-467, (Clineschmidt et al, 1988, supra) or a brain-penetrant antagonist, MK-912, (Pettibone et al, 1987, supra) was associated with emesis in the ferret. In addition, yohimbine was able to trigger the emetic reflex whether or not the route of administration was bypassing the lumen of the gastrointestinal tract.

In the ferret, clonidine was found to prevent emesis induced by PDE4 inhibitors. Consistent with the antagonists studies, it appears that the anti-emetic action of clonidine also involves a peripheral and a central locus of action. Emesis induced by PDE4 inhibitors having a mixed peripheral-central site of action (e.g. RS14203, R-rolipram) as well as that induced by PDE4 inhibitors acting predominantly via a peripheral site of action (e.g. CT-2450) was prevented by clonidine (Robichaud et al, 1999, supra). In apparently contradictory reports, clonidine has been noted to lower the incidence and frequency of vomiting following strabismus surgery in children (3–12 yr) (Mikawa et al, *Can. J. Anaesth.* (1995) 42, 977–981, whereas Kumar et al, *Anaesthesiol. Scand.* (1992) 36, 159–164 reported that, in elderly patients undergoing intraocular surgery, clonidine had no effect on emesis despite the fact that it induced sedation (an alpha-2 adrenoceptor agonist-mediated response).

There remains a need in the art for an effective therapy for the treatment or prevention of emesis. In accordance with the present invention, alpha-2 adrenoceptor agonists may be employed to treat and/or prevent emesis, as evidenced by the disclosure herein. Surprisingly, an alpha-2 adrenoreceptor agonist provide an effective therapy for the treatment or prevention of emesis. Such compounds exhibit unexpected and advantageous results, for example, by minimizing the side effects in the prevention or treatment emesis.

Accordingly, the present invention provides a method for the treatment and/or prevention of emesis which comprises administering to a patient in need of such treatment an effective amount of an alpha-2 adrenoceptor agonist. Although the present invention is not limited to a specific mechanism of action, the inventors postulate that the activity of an alpha-2 adrenoreceptor agonist provides efficacy in treatment or prevention of emesis.

SUMMARY OF THE INVENTION

The present invention is directed to the use of a class of adrenergic receptor agonists in therapy. More particularly, this invention is concerned with methods for using an alpha-2 adrenoceptor agonist alone or in combination with other antiemetic agents for the treatment and/or prevention of emesis.

DESCRIPTION OF THE INVENTION

The present invention relates to methods for the treatment or prevention of emesis by administering an alpha-2 adrenoreceptor agonist. The present invention further relates to methods for the treatment or prevention of emesis in a patient which comprises administering an alpha-2 adrenoreceptor agonist.

The present invention further relates to a method for the treatment or prevention of emesis in a patient which comprises administering an alpha-2 adrenoreceptor agonist, wherein the alpha-2 adrenoreceptor agonist minimize the side effects of nausea and/or emesis associated with other pharmacological agents.

The present invention accordingly provides the use of an alpha-2 adrenoreceptor agonist for the manufacture of a medicament for the treatment or prevention of emesis.

In a further aspect of the present invention, there is provided a pharmaceutical composition for the treatment or prevention of emesis comprising an alpha-2 adrenoreceptor agonist, together with at least one pharmaceutically acceptable carrier or excipient.

As used herein, the term "emesis" will be understood to include nausea and vomiting. The alpha-2 adrenoceptor agonists of use in the present invention are beneficial in the therapy of acute, delayed or anticipatory emesis, including emesis induced by chemotherapy, radiation, toxins, viral or bacterial infections, pregnancy, vestibular disorders (e.g. motion sickness, vertigo, dizziness and Meniere's disease), surgery, migraine, and variations in intracranial pressure. The alpha-2 adrenoceptor agonists of use in the invention are of particular benefit in the therapy of emesis induced by radiation, for example during the treatment of cancer, or radiation sickness; and in the treatment of post-operative nausea and vomiting. Most especially, the alpha-2 adrenoceptor agonists of use in the invention are beneficial in the therapy of emesis induced by antineoplastic (cytotoxic) agents including those routinely used in cancer chemotherapy, and emesis induced by other pharmacological agents, for example, alpha-2 adrenoceptor antagonists, such as yohimbine, MK-912 and MK-467, and type IV cyclic nucleotide phosphodiesterase (PDE4) inhibitors, such as RS14203, CT-2450 and rolipram.

Particular examples of chemotherapeutic agents are described, for example, by D. J. Stewart in *Nausea and Vomiting: Recent Research and Clinical Advances*, ed. J. Kucharczyk et al., CRC Press Inc., Boca Raton, Fla., USA, 1991, pages 177–203, especially page 188. Commonly used chemotherapeutic agents include cisplatin, dacarbazine (DTIC), dactinomycin, mechlorethamine (nitrogen mustard), streptozocin, cyclophosphamide, carmustine (BCNU), lomustine (CCNU), doxorubicin (adriamycin), daunorubicin, procarbazine, mitomycin, cytarabine, etoposide, methotrexate, 5-fluorouracil, vinblastine, vincristine, bleomycin and chlorambucil (R. J. Gralle et al. in *Cancer Treatment Reports*, 1984, 68, 163–172).

The present invention is further directed to a method for ameliorating the symptoms attendant to emesis in a patient comprising administering to the patient an alpha-2 adrenoreceptor agonist.

In accordance with the present invention the alpha-2 adrenoreceptor agonist is administered to a patient in a quantity sufficient to treat or prevent the symptoms and/or underlying etiology associated with emesis in the patient.

Although the present invention is useful in any mammal suffering from emesis a preferred subject is a human.

The compounds of use in the present invention are any alpha-2 adrenergic agonists. As used herein, the term "alpha-2 adrenergic agonist" means a compound that binds either to presynaptic alpha-2 receptors on sympathetic post-ganglionic nerve endings or to postsynaptic alpha-2 receptors on smooth muscle cells. The alpha-2 adrenoreceptor agonist may be peptidal or non-peptidal in nature, however, the use of a non-peptidal alpha-2 adrenoreceptor agonist is preferred. In a preferred embodiment, thealpha-2 adrenoreceptor agonist is a CNS-penetrant alpha-2 adrenoreceptor agonist. In addition, for convenience the use of an orally active alpha-2 adrenoreceptor agonist is preferred. To facilitate dosing, it is also preferred that the alpha-2 adrenoreceptor agonist is a long acting alpha-2 adrenoreceptor agonist. An especially preferred class of alpha-2 adrenoreceptor agonists of use in the present invention are those compounds which are orally active and long acting.

Particularly preferred alpha-2 adrenoceptor agonists of use in the present invention possess a high degree of specificity for the alpha-2 adrenoceptor, i.e. their effect on other non-related types of receptors (e.g. beta-adrenoceptors, histamine receptors, etc.) will be negligible. Such compounds may be referred to as "specific alpha-2 adrenoceptor agonists"

Furthermore, especially preferred alpha-2 adrenoceptor agonists of use in the present invention possess a high degree of selectivity for the alpha-2 adrenoceptor, i.e. their effect on other related alpha-adrenoceptors (e.g. alpha-1 adrenoceptors) will be negligible. Such compounds may be referred to as "selective alpha-2 adrenoceptor agonists"

Alpha-2 adrenoreceptor agonists of use in the present invention are fully described, for example, in U.S. Pat. Nos. 4,454,139, 4,473,572, 4,481,200, 4,550,114, 4,604,398, 4,640,924, 4,717,731, 5,914,342, 4,923,865, 5,804,587, 5,916,900 and 5,965,595.

Without limiting the invention to the specific groups and compounds listed, the following is a list of representative alpha-2 adrenergic agonists useful in this invention: imino-imidazolines, including clonidine (U.S. Pat. No. 3,202,660), apraclonidine (U.S. Pat. No. 4,517,199) and brimonidine (UK 14,304; 5-bromo-6-(2-imidazolin-2-ylamino)-quinoxaline); imidazolines, including naphazoline (U.S. Pat. No. 2,161,938), oxymetazoline (German Patent 1,117,588), tetrahydrozoline (U.S. Pat. Nos. 2,842,478 and 2,731,471), and tramazoline (German Patent 1,191,381 and 1,195,323); imidazoles, including detomidine (U.S. Pat. No. 4,443,466), medetomidine (U.S. Pat. No. 4,544,664), and dexmedetomidine (U.S. Pat. No. 5,091,402); azepines, including B-HT 920 (6-allyl-2-amino-5,6,7,8 tetrahydro-4H-thiazolo[4,5-d]-azepine, U.S. Pat. No. 5,030,630) and B-HT 933 (Rubin et al, *J. Cardiovasc. Pharmacol.* (1982) 4, 527–530); thiazines, including xylazine (U.S. Pat. No. 3,235,550); oxazolines, including rilmenidine (U.S. Pat. No. 4,102,890); guanidines, including guanabenz (German Patent 1,804,634) and guanfacine (U.S. Pat. No. 3,632,645); catecholamines, including phenylephrine (U.S. Pat. Nos. 1,932,347 and 1,954,389), mephentermine (U.S. Pat. No. 2,590,079), metaraminol (U.S. Pat. No. 1,995,709), and methoxamine hydrochloride (U.S. Pat. No. 2,359,707).

Analogs of the foregoing compounds that function as alpha-2 adrenergic agonists are also specifically intended to be embraced by the invention. The ability of such analogs to treat and/or prevent emesis according to the invention can be tested easily using no more than routine experimentation (see, for instance, the rabbit aorta ($\alpha_1$-adrenoceptor) and rabbit vas deferens ($\alpha_2$-adrenoceptor) assays described in International (PCT) Publication No. WO 92/04345 and the receptor binding assays described in International (PCT) Publication No. WO 96/35424).

Specific alpha-2 adrenoreceptor agonists of use in the present invention include, but are not limited to, clonidine, —"apraclonidine, para-aminoclonidine, brimonidine, naphazoline, oxymetazoline, tetrahydrozoline, tramazoline, detomidine, medetomidine, dexmedetomidine, B-HT 920, B-HIT 933, xylazine, rilmenidine, guanabenz, guanfacine, labetalol, phenylephrine, mephentermine, metaraminol, methoxamine and xylazine.

In an aspect of the present invention, the alpha-2 adrenoreceptor agonist of use in the present invention is other than clonidine.

Further alpha-2 adrenoceptor agonists of use in the present invention are disclosed in the following patent publications: WO 92/04345, WO 96/35424, WO 98/23591, WO 98/23596, WO 98/23609, WO 98/23610, WO 98/23611, WO 98/23612, WO 98/46595 and WO 99/26942.

A particular class of alpha-2 adrenoceptor agonists of use in the present invention includes compounds of formula (A):

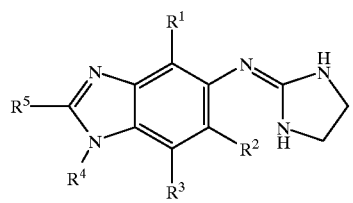

(A)

wherein $R^1$ is hydrogen, $C_{1-3}$alkyl, $C_{2-3}$alkenyl, cyclopropyl or halo;

$R^2$ is hydrogen, $C_{1-3}$alkyl, $C_{2-3}$alkenyl, cyclopropyl, methoxy, cyano or halo;

$R^3$ is hydrogen, $C_{1-3}$alkyl, $C_{2-3}$alkenyl, $C_{2-3}$alkynyl, cyclopropyl, $C_{1-3}$alkylthio, $C_{1-3}$alkoxy, hydroxy, thio, nitro, cyano, amino, $C_{1-3}$alkylamino, $diC_{1-3}$alkylamino or halo;

$R^4$ is hydrogen or $C_{1-3}$alkyl;

$R^5$ is hydrogen, methyl, amino, methoxy, hydroxy, cyano or halo; and any enantiomer, optical isomer, stereoisomer, diastereoisomer, tautomer, addition salt, or biohydrolyzable ester, amide or imide thereof.

A preferred class of compound of formula (A) is that wherein $R^1$ is $C_{1-3}$alkyl or cyclopropyl;

$R^2$ is hydrogen, $C_{1-3}$alkyl, cyclopropyl, methoxy, cyano or halo;

$R^3$ is hydrogen, methyl, hydroxy, cyano or halo;

$R^4$ is hydrogen; and $R^5$ is hydrogen, methyl, amino, methoxy, hydroxy, cyano or halo; and enantiomers, optical isomers, stereoisomers, diastereoisomers, tautomers, addition salts, biohydrolyzable amides and biohydrolyzable esters thereof.

Particularly preferred examples of compounds of formula (A) include:
4,6-dimethyl-5-(2-imidazolinylamino)benzimidazole;
7-cyano-5-(2-imidazolinylamino)-4-methylbenzimidazole;
7-hydroxy-5-(2-imidazolinylamino)-4-methylbenzimidazole;
4-ethyl-5-(2-imidazolinylamino)-7-methylbenzimidazole; and
4-cyclopropyl-5-(2-imidazolinylamino)-7-methylbenzimidazole.

Another particular class of alpha-2 adrenoceptor agonist of use in the present invention includes compounds of formula (B):

(B)

wherein $R_1$ is hydrogen or $C_{1-3}$alkyl;

$R_2$ is hydrogen, $C_{1-3}$alkyl or absent;

$R_3$ is hydrogen, $C_{1-3}$alkyl, amino, hydroxy, mercapto, $C_{1-3}$alkylthio, $C_{1-3}$alkoxy, $C_{1-3}$alkylamino, $diC_{1-3}$alkylamino, cyano or halo;

$R_4$, $R_5$ and $R_7$ are each independently hydrogen, $C_{1-3}$alkyl, $C_{2-3}$alkenyl, $C_{2-3}$alkynyl, cyclopropyl, $C_{1-3}$alkylthio, $C_{1-3}$alkoxy, hydroxy, thio, nitro, cyano, amino, $C_{1-3}$alkylamino, $diC_{1-3}$alkylamino or halo; and when $R_2$ is absent, bond (a) is a double bond;

and enantiomers, optical isomers, stereoisomers, diastereoisomers, tautomers, addition salts, biohydrolyzable amides and biohydrolyzable esters thereof.

Particularly preferred compounds of formula (3) include:
7-ethyl-6-(2-imidazolinylamino)indazole; and
6-(2-imidazolinylamino)-7-methylindazole.

A further particular class of alpha-2 adrenoceptor agonist of use in the present invention includes compounds of formula (C):

(C)

wherein bond (a) is a single or a double bond;

$R_1$ is hydrogen or $C_{1-3}$alkyl;

$R_2$ and $R_3$ are each independently hydrogen, $C_{1-3}$alkyl, $C_{2-3}$alkenyl, $C_{2-3}$alkynyl, cyclopropyl, $C_{1-3}$alkylthio, $C_{1-3}$alkoxy, hydroxy, thio, nitro, cyano, amino, $C_{1-3}$alkylamino, $diC_{1-3}$alkylamino or halo;

$R_4$, $R_5$ and $R_6$ are each independently hydrogen, $C_{1-3}$alkyl, $C_{2-3}$alkenyl, $C_{2-3}$alkynyl, cyclopropyl, $C_{1-3}$alkylthio, $C_{1-3}$alkoxy, hydroxy, thio, nitro, cyano, amino, $C_{1-3}$alkylamino, $diC_{1-3}$alkylamino, halo, or 2-imidazolinylamino; wherein one and only one of $R_4$, $R_5$ and $R_6$ is 2-imidazolinylamino; and $R_7$ is hydrogen, $C_{1-3}$alkyl, $C_{2-3}$alkenyl, $C_{2-3}$alkynyl, cyclopropyl, $C_{1-3}$alkylthio, $C_{1-3}$alkoxy, hydroxy, thio, nitro, cyano, amino, $C_{1-3}$alkylamino, $diC_{1-3}$alkylamino or halo; and enantiomers, optical isomers, stereoisomers, diastereoisomers, tautomers, addition salts, biohydrolyzable amides and biohydrolyzable esters thereof.

Particularly preferred compounds of formula (C) include:
6-(2-imidazolinylamino)-7-methylindole;
3-cyano-6-(2-imidazolinylamino)-7-methylindole;
2,3-dihydro-7-methyl-6-(2-imidazolinylamino)indole;
3-chloro-4-(2-imidazolinylamino)indole;
2,3-dihydro-4-(2-imidazolinylamino)indole;
2,3-dihydro-4-(2-imidazolinylamino)-7-methylindole; and
4-(2-imidazolinylamino)indole.

As used herein, the term "biohydrolyzable ester" refers to an ester of a compound of formula (A), (B) or (C) that is readily converted in vivo by a patient to yield an active compound of use in the present invention.

As used herein, the term "biohydrolyzable amide" refers to an amide of a compound of formula (A), (B) or (C) that is readily converted in vivo by a patient to yield an active compound of use in the present invention.

Further alpha-2 adrenoceptor agonists of use in the present invention include:
[(8-methylquinolin-7-yl)amino]guanidine;
[(4-methylbenzimidazol-5-yl)amino]guanidine;
(4,7-dimethylbenzimidazol-5-yl)guanidine;
(2,4-dimethylbenzimidazol-5-yl)guanidine;
(1,4-dimethylbenzimidazol-5-yl)guanidine;
(4-bromobenzimidazol-5-yl)guanidine;
$N^1$-methyl-$N^2$-(4-methylbenzimidazol-5-yl)guanidine;
(8-methylquinolin-7-yl)guanidine;
(8-bromoquinolin-7-yl)guanidine;
(6-methylbenzothiazol-5-yl)guanidine;
(4-bromobenzothiazol-5-yl)guanidine;
(4-methylbenzothiazol-5-yl)guanidine;
5-(2-imidazolinylamino)-4-methylbenzoxazole;
4-ethyl-5-(2-imidazolinylamino)benzoxazole;
5-(2-imidazolinylamino)-4-methylbenzothiazole;
5-(2-imidazolinylamino)-4-methoxybenzothiazole;
7-cyano-5-(2-imidazolinylamino)-4-methylbenzothiazole;
4,7-dimethyl-6-(2-imidazolinylamino)benzothiazole;
4-cyclopropyl-5-(2-imidazolinylamino)benzothiazole;
4-ethenyl-5-(2-imidazolinylamino)benzothiazole; and
4-bromo-5-(2-imidazolinylamino)benzothiazole;
and pharmaceutically acceptable salts thereof.

The preparation of the such compounds is fully described in patents and publications mentioned herein and known in the art.

Suitable pharmaceutically acceptable salts of the compounds of use in the present invention include acid addition salts which may, for example, be formed by mixing a solution of the compound with a solution of a pharmaceutically acceptable non-toxic acid such as hydrochloric acid, fumaric acid, maleic acid, succinic acid, acetic acid, citric acid, tartaric acid, carbonic acid, phosphoric acid or sulfuric acid. Salts of amine groups may also comprise the quaternary ammonium salts in which the amino nitrogen atom carries an alkyl, alkenyl, alkynyl or aralkyl group. Where the compound carries an acidic group, for example a carboxylic acid group, the present invention also contemplates salts thereof, preferably non-toxic pharmaceutically acceptable salts thereof, such as the sodium, potassium and calcium salts thereof.

The above compounds are only illustrative of the alpha-2 adrenoreceptor agonists which are currently under investigation. As this listing of compounds is not meant to be comprehensive, the methods of the present invention may employ any alpha-2 adrenoreceptor agonist. Accordingly, the present invention is not strictly limited to any particular structural class of compound.

The identification of a compound as an alpha-2 adrenoreceptor agonist, and thus able to have utility in the present invention may be readily determined without undue experimentation by methodology well known in the art.

The alpha-2 adrenoreceptor agonists employed in the present invention are also useful for the treatment of or prevention of emesis in conjunction with the use of other antiemetic agents known in the art.

Suitable classes of other antiemetic agents of use in conjunction with the present invention include, for example, a 5-$HT_3$ antagonist such as ondansetron, granisetron or tropisetron; a dopamine antagonist such as metoclopramide or domperidone; an anticholinergic agent such as scopolamine; a $GABA_B$ receptor agonist such as baclofen; an $NK_1$ receptor antagonist as described, for example, in EP-A-0436334, EP-A-0443132, EP-A-0532456, EP-A-0591040, WO 92/17449, WO 93/21155, WO 95/08549, WO 95/14017, WO 95/16679, WO 95/18124, WO 95/23798, or WO 97/49710; or a $GABA_A$ $\alpha_2$ and/or $\alpha_3$ receptor agonist as described in WO 98/04559, WO 99/67245 or WO 99/37644.

The alpha-2 adrenoreceptor agonist may be administered alone or in combination by oral, parenteral (e.g., intramuscular, intraperitoneal, intravenous or subcutaneous injection, or implant), nasal, vaginal, rectal, sublingual, or topical routes of administration and can be formulated in dosage forms appropriate for each route of administration.

Preferably the compositions according to the present invention are in unit dosage forms such as tablets, pills, capsules, powders, granules, solutions or suspensions, or suppositories, for oral, parenteral or rectal administration, by inhalation or insufflation or administration by trans-dermal patches or by buccal cavity absorption wafers.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the novel compositions of the present invention may be incorporated for administration orally or by injection include aqueous solutions, suitably flavoured syrups, aqueous or oil suspensions, and flavoured emulsions with edible oils such as cottonseed oil, sesame oil, coconut oil, peanut oil or soybean oil, as well as elixirs and similar pharmaceutical vehicles. Suitable dispersing or suspending agents for aqueous suspensions include synthetic and natural gums such as tragacanth, acacia, alginate, dextran, sodium carboxymethylcellulose, methylcellulose, polyvinyl-pyrrolidone or gelatin.

Preferred compositions for administration by injection include those comprising an alpha-2 adrenoreceptor agonist as the active ingredient, in association with a surface-active agent (or wetting agent or surfactant) or in the form of an emulsion (as a water-in-oil or oil-in-water emulsion).

Suitable surface-active agents include, in particular, non-ionic agents, such as polyoxyethylenesorbitans (e.g. Tween 20, 40, 60, 80 or 85) and other sorbitans (e.g. Span 20, 40, 60, 80 or 85). Compositions with a surface-active agent will conveniently comprise between 0.05 and 5% surface-active agent, and preferably between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid, Liposyn, Infonutrol, Lipofundin and Lipiphysan. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion will preferably comprise fat droplets between 0.1 and 1.0 μm, particularly 0.1 and 0.5 μm, and have a pH in the range of 5.5 to 8.0.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. Preferably the compositions are administered by the oral or nasal respiratory route for local or systemic effect. Compositions in preferably sterile pharmaceutically acceptable solvents may be nebulised by use of inert gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compositions of the present invention may also be presented for administration in the form of trans-dermal patches using conventional technology. The compositions may also be administered via the buccal cavity using, for example, absorption wafers.

Compositions in the form of tablets, pills, capsules or wafers for oral administration are particularly preferred.

As noted, the compounds employed in the present invention are also useful for the treatment of or prevention of emesis in conjunction with another antiemetic agents known in the art, such as a 5-HT$_3$ antagonist, a dopamine antagonist, an anticholinergic agent, a GABA$_B$ receptor agonist, an NK$_1$ receptor antagonist, and a GABA$_A$ α$_2$ and/or α$_3$ receptor agonist.

It will be appreciated that when using a combination of the present invention, the alpha-2 adrenoreceptor agonist and the other antiemetic agent will be administered to a patient, within a reasonable period of time. The compounds may be in the same pharmaceutically acceptable carrier and therefore administered simultaneously. They may be in separate pharmaceutical carriers such as conventional oral dosage forms which are taken simultaneously. The term "combination" also refers to the case where the compounds are provided in separate dosage forms and are administered sequentially.

When administered in combination, either as a single product or as separate pharmaceutical compositions, the alpha-2 adrenoceptor agonist and the other antiemetic medicament are to be presented in a ratio which is consistent with the manifestation of the desired effect. In particular, the ratio by weight of the alpha-2 adrenoceptor agonist and the other antiemetic agent will suitably be between 0.001 to 1 and 1000 to 1, and especially between 0.01 to 1 and 100 to 1.

The present invention also provides a pharmaceutical product comprising (i) an alpha-2 adrenoceptor agonist; and (ii) one or more antiemetic medicaments selected from the group consisting of 5-HT$_3$ antagonists, dopamine antagonists, anticholinergic agents, GABA$_B$ receptor agonists, NK$_1$ receptor antagonists, and GABA$_A$ α$_2$ and/or α$_3$ receptor agonists; for simultaneous, separate or sequential administration. The preferred alpha-2 adrenoceptor agonists for use in these pharmaceutical products are the same as the preferred alpha-2 adrenoceptor agonists disclosed herein for use in emesis.

The dosage of active ingredient in the compositions of this invention may be varied, however, it is necessary that the amount of the active ingredient be such that a suitable dosage form is obtained. The active ingredient may be administered to patients (animals and human) in need of such treatment in dosages that will provide optimal pharmaceutical efficacy. The selected dosage depends upon the desired therapeutic effect, on the route of administration, and on the duration of the treatment. The dose will vary from patient to patient depending upon the nature and severity of disease or disorder, the patient's weight, special diets then being followed by a patient, concurrent medication, the intrinsic tachykinin receptor antagonist activity of the compound, the bioavailability upon oral administration of the compound and other factors which those skilled in the art will recognize.

In the treatment of a condition in accordance with the present invention, an appropriate dosage level will generally be about 0.01 mg to 2000 mg per day which may be administered in single or multiple doses. A suitable dosage level for the alpha-2 adrenoceptor agonist is about 0.05 to 1500 mg per day, preferably about 0.25 to 1500 mg per day, and especially about 0.25 to 500 mg per day. The compounds may be administered on a regimen of up to 6 times per day, preferably 1 to 4 times per day, especially 2 times per day and most especially once daily. A suitable dosage level for the other antiemetic medicament will be dependent upon the choice of agent. In general, the compounds may be administered on a regimen of up to 6 times per day, preferably 1 to 4 times per day, especially 2 times per day and most especially once daily.

Pharmaceutical compositions of the present invention may be provided in a solid dosage formulation preferably comprising about 0.05 mg to 500 mg active ingredient. The pharmaceutical composition is preferably provided in a solid dosage formulation comprising about 100 μg, 1 mg, 5 mg, 10 mg, 25 mg, 50 mg, 100 mg, 200 mg or 300 mg active ingredient. Naturally, these dose ranges may be adjusted on a unit basis as necessary to permit divided daily dosage and, as noted above, the dose will vary depending on the nature and severity of the disease, weight of patient, special diets and other factors. The compounds may be formulated into pharmaceutical compositions as known in the art and as discussed herein.

It will be appreciated that the amount of the alpha-2 adrenoreceptor agonist in a patient will vary not only with the particular compounds or compositions selected but also with the route of administration, the nature of the condition being treated, and the age and condition of the patient, and will ultimately be at the discretion of the patient's physician or pharmacist. The length of time during which a tachykinin receptor antagonist will be given varies on an individual basis.

The present invention accordingly provides the use of an alpha-2 adrenoreceptor agonist for the manufacture of a medicament adapted for oral administration for treating or preventing emesis in a patient.

The present invention also provides a method for treating or preventing emesis or ameliorating the symptoms attendant to emesis in a patient, which method comprises the oral administration to a patient in need of such treatment of an effective amount of an alpha-2 adrenoreceptor agonist.

In a further aspect of the present invention, there is provided an oral pharmaceutical composition for treating or preventing emesis in a patient, which comprises an alpha-2 adrenoreceptor agonist, together with a pharmaceutically acceptable carrier or excipient.

It will be appreciated to those skilled in the art that reference herein to treatment extends to prophylaxis (prevention) as well as the treatment of the noted diseases/disorders and symptoms. Because the specific diagnosis of depression and/or anxiety in a particular patient may be difficult, the patient may benefit from the prophylactic administration of a subject compound in accordance with the present invention.

The following examples are provided for the purpose of further illustration only and are not intended to be limitations on the disclosed invention.

EXAMPLE 1
Alpha-2 Adrenoreceptor Activity

The alpha-2 selectivity of a compound may be determined by measuring receptor binding affinities and in vitro functional potencies in a variety of tissues known to possess alpha-2 and/or alpha-1 receptors. (See, e.g., The Alpha-2 Adrenergic Receptors, L. E. Limbird, ed., Humana Press, Clifton, N.J.) The following in vivo assays are typically conducted in rodents or other species. Central nervous system activity is determined by measuring locomotor activity as an index of sedation. (See, e.g., Spyraki, C. & H. Fibiger, "Clonidine-induced Sedation in Rats: Evidence for Mediation by Postsynaptic Alpha-2 Adrenoreceptors", Journal of Neural Transmission, Vol. 54 (1982), pp. 153–163).

EXAMPLE 2
Ferret Emesis: Alpha-2 Adrenoreceptor Agonists

The anti-emetic activity of alpha-2 adrenoceptor agonists is preferably measured using, for instance, an in vivo emesis assay in the ferret. A variety of emetic stimuli may be employed including, for example, treatment with type IV cyclic nucleotide phosphodiesterase (PDE4) inhibitors (see Robichaud et al, *Neuropharmacology* (1999) 38, 289–297).

Male adult ferrets (*Mustela putorius furo;* 1–2 kg, Marshall Farms, North Rose, N.Y., U.S.A.) were used and experiments were conducted according to procedures previously described (Robichaud et al, 1999, supra). The ferrets were housed in a humidity and temperature controlled environment with food (Marshall Premium ferret diet; Marshall Farms, North Rose, N.Y., U.S.A.) and water provided ad libitum. On the day of the experiment, ferrets were put into individual cages and left to habituate for at least 30 minutes. Fasting was not a pre-requisite of these experiments. Pre-treatment with a test compound or vehicle was performed using a subcutaneous, an intraperitoneal or an oral administration, 60 minutes prior to the emetic challenge. Emesis was induced by PDE4 inhibitors administered orally (dosing volume=1 ml/kg) at a dose known to cause emesis (Robichaud et al, 1999, supra). Drugs were freshly prepared on the day of the experiment. PDE4 inhibitors were dissolved in 100% polyethylene glycol (PEG; MW 200) whereas clonidine and yohimbine were dissolved in saline. Following the administration of the test compound, the animals were observed continuously up to 120 minutes post-PDE4 inhibitor dosing. During that time, the number of retches (i.e. rhythmic contraction of the abdomen) and vomiting movements (i.e. oral expulsion or attempt to expel solid/liquid matter from the gastrointestinal tract) were recorded.

Ferrets were pre-treated with the $alpha_2$-adrenoceptor antagonist, yohimbine. Following an intraperitoneal injection, yohimbine induced retching and vomiting in all ferrets treated rapidly after dosing. A similar effect was observed whether the drug was administered orally or subcutaneously. Emesis was also recorded following the administration of two other selective $alpha_2$-adrenoceptor antagonists: MK-912 and MK-467 (Pettibone et al., 1987; Clineschmidt et al., 1988). The $alpha_2$-adrenoceptor agonist, clonidine, was administered to ferrets at doses ranging from 62.5–250 $\mu g\ kg^{-1}$. By itself, clonidine did not trigger emesis. However, a light sedation that appeared to be dose-related was rapidly seen following the administration. Upon challenge with an emetic dose of the PDE4 inhibitor RS14203 (1 mg $kg^{-1}$, p.o.), clonidine dose-dependently decreased the number of retches and vomits induced by RS14203 and increased the latency of onset. At the highest dose tested (250 $\mu g\ kg^{-1}$), five out of six animals pre-treated with clonidine showed complete protection against RS14203-induced emesis. The animal that did express an emetic response in that particular group experienced one retching and one vomiting episode. Similarly, clonidine (250 $\mu g\ kg^{-1}$) also abolished emesis induced by CT-2450 (30 mg $kg^{-1}$, p.o.) in all animals treated and provided complete protection in two out of three animals challenged with an emetic dose of R-rolipram (3 mg $kg^{-1}$, p.o.). The administration of RS14203 to ferrets produced in addition to emesis some other behavioural effects such as salivation, hyperventilation, gagging and clawing at the mouth (Table 3). These effects can be seen with a number of inhibitors of PDE4. In the clonidine pre-treated group (250 $\mu g$/kg), none of the animals experienced salivation and one out of six showed hyperventilation following RS14203 administration. Clonidine had no effect on RS14203-induced gagging or clawing at the mouth.

TABLE 1

Administration of alpha-2 adrenoceptor antagonists to ferrets

| Treatment | Retches (n° episodes) | Vomits (n° episodes) | Latency responders only (min) | Incidence (n° responders) /n° tested) |
|---|---|---|---|---|
| Vehicle (i.p.) | 0 | 0 | — | 0/3 |
| Yohimbine (3 mg/kg i.p.) | 18.7 ± 3.8 | 5.3 ± 1.8 | 7 ± 1 | 3/3 |
| Vehicle (p.o.) | 0 | 0 | — | 0/3 |
| Yohimbine (3 mg/kg p.o.) | 9.8 ± 6.2 | 3.2 ± 1.2 | 30.3 ± 13.4 | 3/4 |
| Vehicle (s.c.) | 0 | 0 | — | 0/3 |
| Yohimbine (3 mg/kg s.c.) | 29.7 ± 17.6 | 3.0 ± 1.7 | 9.5 ± 2.5 | 2/3 |
| Vehicle (p.o.) | 0 | 0 | — | 0/3 |
| MK-912 (1 mg/kg p.o.) | 3.2 ± 2.3 | 0.4 ± 0.3 | 13.0 ± 5.0 | 2/8 |

TABLE 1-continued

Administration of alpha-2 adrenoceptor antagonists to ferrets

| Treatment | Retches (n° episodes) | Vomits (n° episodes) | Latency responders only (min) | Incidence (n° responders) /n° tested) |
|---|---|---|---|---|
| Vehicle (p.o.) | 0 | 0 | — | 0/3 |
| MK-467 | | | | |
| (1 mg/kg p.o.) | 0 | 0 | — | 0/3 |
| (3 mg/kg p.o.) | 4 ± 4 | 0.3 ± 0.3 | 12 | 1/3 |
| (10 mg/kg po) | 12 ± 6 | 1.3 ± 0.9 | 18.5 ± 2.5 | 2/3 |

Saline was the vehicle used for yohimbine and 100% PEG was used for MK-912 and MK-467. Data is expressed as mean±SEM.

TABLE 2

Effect of clonidine on emesis induced by PDE4 inhibitors in ferrets

| Pre-treatment (all s.c.) | Retches (n° episodes) | Vomits (n° episodes) | Latency responders only (min) | Incidence (n° episodes) /n° tested) |
|---|---|---|---|---|
| Emetic agent: RS14203 (1 mg/kg; p.o.) | | | | |
| vehicle | 29.8 ± 5.9 | 4.8 ± 0.9 | 10.5 ± 5.3 | 6/6 |
| clonidine | | | | |
| (62.5 µg/kg) | 9.3 ± 7.9 | 1.7 ± 1.2 | 55.0 ± 49.0 | 2/3 |
| (125 µg/kg) | 2 ± 2* | 1 ± 1* | 72 | 1/3 |
| (250 µg/kg) | 0.2 ± 0.2* | 0.2 ± 0.2* | 111 | 1/6 |
| Emetic agent: CT-2450 (30 mg/kg; p.o.) | | | | |
| vehicle | 24.4 ± 8.6 | 4.0 ± 1.4 | 21.25 ± 5.34 | 4/5 |
| clonidine | 0* | 0* | — | 0/5 |
| (250 µg/kg) | | | | |
| Emetic agent: R-rolipram (3 mg/kg; p.o.) | | | | |
| vehicle | 18.3 ± 3.0 | 2.7 ± 0.3 | 25.7 ± 19.8 | 3/3 |
| clonidine | 54.3 ± 54.3 | 5.7 ± 5.7 | 5 | 1/3 |
| (250 µg/kg) | | | | |

The animals were pre-treated 60 minutes prior to an emetic provocation with PDE4 inhibitors and emesis was monitored for 2 hours thereafter. Saline was the vehicle used for clonidine and 100% PEG was used for PDE4 inhibitors. Data is expressed as mean ± SEM.
*Statistical difference from vehicle group at p < 0.05.

TABLE 3

Effect of clonidine on behavioural effects observed following the administration of RS14203 (1 mg/kg. p.o.) in ferrets (n° responders/n° tested)

| Pre-treatment (all s.c.) | Salivation | Hyperventilation | Gagging | Clawing at mouth |
|---|---|---|---|---|
| Vehicle | 6/6 | 6/6 | 6/6 | 6/6 |
| Clonidine | | | | |
| (62.5 µg/kg) | 2/3 | 2/3 | 1/3 | 2/3 |
| (125 µg/kg) | 1/3 | 2/3 | 1/3 | 1/3 |
| (250 µg/kg) | 0/6 | 1/6 | 5/6 | 5/6 |

As demonstrated in the foregoing study, emesis induced by PDE4 inhibitors was prevented by a pre-treatment with the alpha-2 adrenoreceptor agonist clonidine. These results suggest that an alpha-2 adrenoreceptor agonist may be employed to minimize the side effects of nausea and/or emesis, such as associated with administration of a PDE4 inhibitor.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A method for the treatment of emesis induced by a chemotherapeutic agent in a patient in need thereof which comprises administering to the patient an alpha-2 adrenoreceptor agonist, which is other than clonidine.

2. The method of claim 1 wherein the alpha-2 adrenoreceptor agonist is a specific alpha-2 adrenoceptor agonist.

3. The method of claim 1 wherein the alpha-2 adrenoreceptor agonist is a selective alpha-2 adrenoceptor agonist.

4. The method of claim 1 wherein the patient is a human.

5. A method for the prevention of emesis induced by a chemotherapeutic agent in a patient in need thereof which comprises administering to the patient an alpha-2 adrenoreceptor agonist, which is other than clonidine.

6. The method of claim 5 wherein the alpha-2 adrenoreceptor agonist is a specific alpha-2 adrenoceptor agonist.

7. The method of claim 5 wherein the alpha-2 adrenoreceptor agonist is a selective alpha-2 adrenoceptor agonist.

8. The method of claim 5 wherein the patient is a human.

9. A method for ameliorating the symptoms attendant to emesis induced by a chemotherapeutic agent in a patient comprising administering to the patient in need thereof an alpha-2 adrenoreceptor agonist, which is other than clonidine.

10. The method of claim 9 wherein the alpha-2 adrenoreceptor agonist is a specific alpha-2 adrenoceptor agonist.

11. The method of claim 9 wherein the alpha-2 adrenoreceptor agonist is a selective alpha-2 adrenoceptor agonist.

12. The method of claim 9 wherein the patient is a human.

13. A method for the prevention of emesis induced by a chemotherapeutic agent in a patient in need thereof which comprises administering to the patient an alpha-2 adrenoreceptor agonist, which is other than clonidine, and an antiemetic agent.

14. The method of claim 13 wherein the antiemetic agent is a compound selected from the group consisting of: a 5-$HT_3$ antagonist, a dopamine antagonist, an anticholinergic agent, a $GABA_B$ receptor agonist, an $NK_1$ receptor antagonist, and a $GABA_A$ $\alpha_2$ and/or $\alpha_3$ receptor agonist.

15. The method of claim 13 wherein the antiemetic agent is a 5-$HT_3$ antagonist.

* * * * *